United States Patent [19]

Osaka et al.

[11] Patent Number: 4,933,066
[45] Date of Patent: Jun. 12, 1990

[54] APPARATUS FOR MOUNTING A DIFFUSION-LIMITING MEMBRANE FOR A SENSOR

[75] Inventors: Tatsuhiko Osaka, Kurita; Hiroshi Terawaki, Kouka; Toji Mukai, Yasu; Koichi Yamasaki, Oumihachiman, all of Japan

[73] Assignee: Daikin Industries, Ltd., Osaka, Japan

[21] Appl. No.: 423,567

[22] Filed: Oct. 16, 1989

Related U.S. Application Data

[63] Continuation of Ser. No. 176,288, Mar. 31, 1988, abandoned.

[30] Foreign Application Priority Data

| Mar. 31, 1987 | [JP] | Japan | 62-49737 |
| Dec. 15, 1987 | [JP] | Japan | 62-191216 |
| Dec. 15, 1987 | [JP] | Japan | 62-191215 |
| Dec. 26, 1987 | [JP] | Japan | 62-197712 |
| Dec. 26, 1987 | [JP] | Japan | 62-197705 |
| Dec. 26, 1987 | [JP] | Japan | 62-197707 |
| Dec. 26, 1987 | [JP] | Japan | 62-197704 |
| Dec. 26, 1987 | [JP] | Japan | 62-197706 |

[51] Int. Cl.$^5$ .......................... G01N 27/30
[52] U.S. Cl. .................. 204/403; 435/291; 435/817
[58] Field of Search .......... 204/403, 1 E, 407, 402, 204/415; 435/817, 291, 288

[56] References Cited

U.S. PATENT DOCUMENTS

4,757,022  7/1988  Shults et al. .............. 435/291

Primary Examiner—G. L. Kaplan

[57] ABSTRACT

An apparatus for mounting a diffusion-limiting membrane for a sensor in which a mounting member for mounting a diffusion-limiting membrane holding plate is movable toward and away from an enzyme electrode unit and in which, with the mounting member positioned away from the enzyme electrode unit, a diffusion-limiting membrane holding plate having a diffusion-limiting membrane mounted thereon is mounted on or removed from the mounting member, thus preventing the diffusion-limiting membrane from being slidingly rubbed with the surface of the enzyme electrode and in which, with the holding plate mounted on the mounting member, the mounting member ius moved toward the enzyme electrode unit, causing the diffusion-limiting membrane to be stuck to the surface of the enzyme electrode unit.

24 Claims, 14 Drawing Sheets

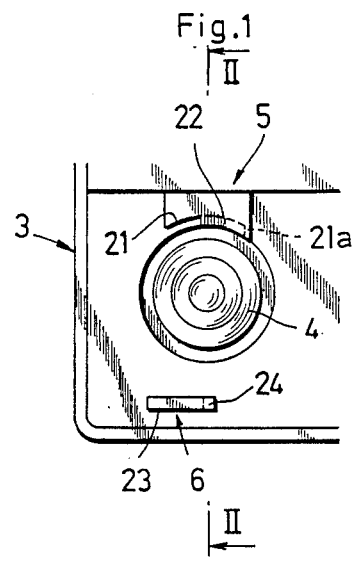
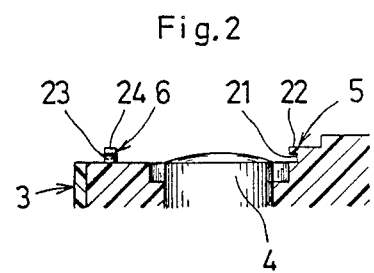
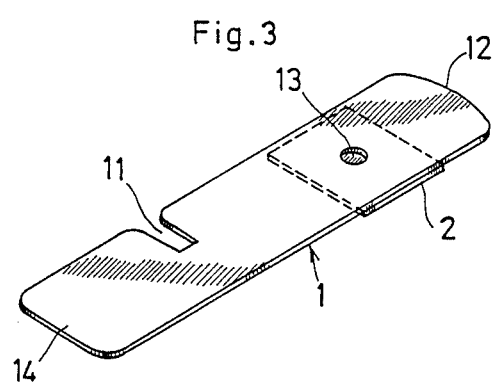
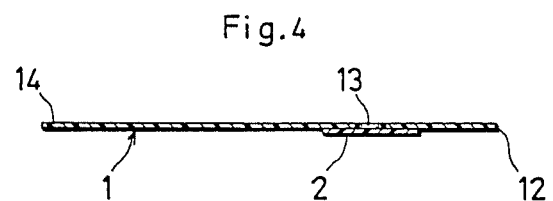

APPARATUS FOR MOUNTING A DIFFUSION-LIMITING MEMBRANE FOR A SENSOR

This application is a continuation of application Ser. No. 07/176,288 filed Mar. 31, 1988 and now abandoned.

BACKGROUND OF THE INVENTION

The present invention relates to an apparatus for mounting a diffusion-limiting membrane for a sensor, and more particularly to an apparatus for mounting a diffusion-limiting membrane for a sensor suitably adapted to stick a diffusion-limiting membrane to be replaced as necessary, to the surface of an enzyme electrode unit of a sensor.

It is known that a physiologic active substance has a characteristic capable of selectively detecting a very complicated organic compound, protein or the like with high sensibility. With attention directed to this characteristic, researches and developments have been made on measurement of such organic compound, protein or the like with the use of an enzyme electrode unit having base electrodes on which a physiologic active substance is immobilized.

In particular, a sensor incorporating the enzyme electrode above-mentioned is suitable for a biochemical analysis of the components of body fluids for clinical analysis or prevention of a disease. This accelerates the researches and developments above-mentioned.

When measuring a target substance with the use of the enzyme electrode unit above-mentioned, the target substance is oxidized or reduced under the presence of a physiologic active substance. The concentration of the target substance is determined by measuring the amount of a substance produced or consumed in such oxidation or reduction. Accordingly, the upper limit of concentration which can be measured, is determined dependent on the amount of a substance provoking such oxidation or reduction, for example the amount of oxygen.

In view of the foregoing, it has been proposed to increase the concentration measuring limit by limiting the penetration rate of a target substance by a diffusion-limiting membrane mounted on the surface of an enzyme-immobilized membrane in/on which a physiologic active substance is immobilized.

By way of example, the following description will describe a measurement of glucose concentration with the use of a glucose sensor.

As shown in FIG. 26, the glucose sensor has a base stand 91, an electrode unit body 92 disposed at a predetermined position of the base stand 91, and a wetting liquid holding portion (not shown) which is press-contacted with the electrode unit body 92 to maintain the same wet and active. The electrode unit body 92 has base electrodes 93, a glucose oxidase immobilized membrane 94 (hereinafter referred to as the GOD immobilized membrane) covering the base electrodes 93, and a diffusion-limiting membrane 95 covering the GOD immobilized membrane 94. The sensor also has a cap 96 for pressing the GOD immobilized membrane 94 and the diffusion-limiting membrane 95 to the surfaces of the base electrodes 93. The cap 96 integrally holds the diffusion-limiting membrane 95.

When a glucose concentration measurement is not to be made, the wetting liquid holding portion may be pressed to the electrode unit body 92 to maintain the electrode unit body 92 wet. This maintains the GOD immobilized membrane 94 active, thus keeping the sensor ready for an accurate measurement of glucose concentration.

When a glucose concentration measurement is to be made, pressing the wetting liquid holding portion to the electrode unit body 92 is released. Then, a target solution to be measured, for example blood, may be dropped on the diffusion-limiting membrane 95. Large-diameter particles such as blood corpuscles are prevented from entering the GOD immobilized membrane 94, and small-diameter particles only reach to the same. Among the small-diameter particles which have reached to the GOD immobilized membrane 94, glucose is oxidized under the presence of glucose oxidase (hereinafter referred to as GOD) and oxygen to produce gluconic acid and hydrogen peroxide. Through the base electrodes 93, an electric signal corresponding to the amount of the hydrogen peroxide thus produced or the remaining oxygen may be taken out. Based on the electric signal thus taken out, an accurate measurement of the concentration of glucose in blood may be made.

However, when continuously making a number of measurements of the concentration of glucose in bloods of a large number of people, it is required to drop each blood on the diffusion-limiting membrane 95 for every measurement. It is also required to replace the diffusion-limiting membrane which has become clogged due to a plurality of measurements, thereby to prevent the glucose penetration ratio from being lowered more than a predetermined rate. Such replacement involves a replacement of the diffusion-limiting membrane 95 integrally mounted on the electrode unit body 92. Further required is a uniform mounting of a new diffusion-limiting membrane 95 on the GOD immobilized membrane 94. This disadvantageously takes a lot of working time. Further, even though the diffusion-limiting membrane is replaced with great care used, the mounting condition may vary more or less to produce variations in measured data.

When the electrode unit body 92 has a small diameter, resulting in decrease in the cap 96, this causes the manual operation for replacement of the diffusion-limiting membrane 95 to be very difficult. This makes the problems above-mentioned more conspicuous.

Moreover, the diffusion-limiting membrane 95 is mounted on the cap 96, requiring a large space for preserving and/or transporting the same.

The description hereinbefore which has discussed mainly the case of measuring the concentration of glucose, may be also applied to the case of measuring the concentrations of other substances in blood, or the case of measuring the concentrations of substances in other body fluids than blood, such as urine.

SUMMARY OF THE INVENTION

It is an object of the present invention to provide an apparatus for mounting a diffusion-limiting membrane for a sensor which remarkably simplifies the mounting-/removal of a diffusion-limiting membrane.

It is another object of the present invention to provide an apparatus for mounting a diffusion-limiting membrane for a sensor which assures a uniform adhesion of a diffusion-limiting membrane to the enzyme-immobilized membrane.

It is a further object of the present invention to provide an apparatus for mounting a diffusion-limiting membrane for a sensor which considerably restrains the deterioration in the activity of a physiologic active substance immobilized in/on the membrane.

It is still another object of the present invention to provide an apparatus for mounting a diffusion-limiting membrane for a sensor which also simplifies a replacement of the membrane in/on which a physiologic active substance is immobilized.

It is a still further object of the present invention to provide an apparatus for mounting a diffusion-limiting membrane for a sensor which eliminates the danger that disease germs may stick to the operator when a target solution to be measured is a body fluid.

It is yet another object of the present invention to provide an apparatus for mounting a diffusion-limiting membrane for a sensor which facilitates cleaning of a mounting member for mounting a diffusion-limiting membrane holding plate.

In order to achieve the objects above-mentioned, the apparatus for mounting a diffusion-limiting membrane for a sensor in accordance with the present invention comprises:

a pair of positioning portions disposed on a sensor having an enzyme electrode unit having an enzyme-immobilized membrane in/on which a physiologic active substance is immobilized, said pair of positioning portions being opposite to each other with respect to the enzyme electrode unit; and a resilient thin plate adapted to be engaged with the pair of positioning portions, causing the resilient thin plate to be resiliently bent to come in contact with the enzyme electrode unit;

the resilient thin plate having an opening in the position thereof which is adapted to be opposite to the enzyme electrode unit when the resilient thin plate is mounted on the sensor, the opening being covered by a diffusion-limiting membrane secured to the resilient thin plate.

The pair of positioning portions may be immovably attached to the sensor. Preferably, one of the pair of positioning portions is immovably attached to the sensor, while the other positioning portion is vertically movably attached to the sensor.

In accordance with the apparatus for mounting a diffusion-limiting membrane for a sensor having the arrangement above-mentioned, the resilient thin plate having a diffusion-limiting membrane attached thereto so as to cover the opening is engaged with the pair of positioning portions opposite to each other with respect to the enzyme electrode. This causes the resilient thin plate to be resiliently bent along the surface of the enzyme electrode unit. This not only enables the diffusion-limiting membrane to be stuck to the surface of the enzyme electrode unit, but also enables the opening to be opposite to the enzyme electrode unit.

Accordingly, when a target solution to be measured is dropped through the opening, a target substance to be measured in the target solution is limited in diffusion to the enzyme-immobilized membrane. Therefore, if the concentration of the target substance to be measured is low, the measuring sensitivity is lowered. However, if the concentration of the target substance to be measured is high, the saturation of an electric output is delayed, thereby to increase the limit of concentration which can be measured.

If a measurement has been made for a target solution containing interfering substances having particle-diameters greater than that of a target substance to be measured, such interfering substances stick to the diffusion-limiting membrane. This causes the diffusion-limiting effect for the target substance to be excessively increased. Disengagement of the resilient thin plate from the pair of positioning portions permits the diffusion-limiting membrane to be removed together with the resilient thin plate.

Thereafter, a new resilient thin plate may be mounted on the enzyme electrode unit, enabling to make a measurement of a target substance with no influence exerted by interfering substances.

When the pair of positioning portions are immovably attached to the sensor, the resilient thin plate as engaged with one positioning portion is engaged with the other positioning portion while being resiliently bent along the enzyme electrode unit. Thus, the diffusion-limiting membrane on the resilient thin plate may be mounted on the sensor.

When one of the positioning portions is immovably attached to the sensor while the other is vertically movably attached to the sensor, with the other positioning portion lifted the resilient thin plate may be engaged with the positioning portions without being resiliently bent. With the resilient thin plate engaged with the positioning portions, the other positioning portion may be lowered to allow the resilient thin plate to be resiliently bent along the surface of the enzyme electrode unit. Thus, the diffusion-limiting membrane on the resilient thin plate may be stuck to the surface of the enzyme electrode unit.

Other objects, advantages and novel characteristics of the present invention will be apparent from the following description.

BRIEF DESCRIPTION OF THE DRAWINGS

FIG. 1 is a plan view of main portions of an apparatus for mounting a diffusion-limiting membrane for a sensor in accordance with a first embodiment of the present invention;

FIG. 2 is a section view taken along the line II—II in FIG. 1;

FIG. 3 is an exploded perspective view of an example of a diffusion-limiting membrane holding plate used in the apparatus for mounting a diffusion-limiting membrane for sensor in accordance with the present invention;

FIG. 4 is a longitudinal section view of the center portion of the holding plate in FIG. 3;

FIG. 22 (B) is a longitudinal section view of FIG. 22 (A);

FIG. 24 (D) is a back perspective view showing the shape of the sponge;

DETAILED DESCRIPTION OF THE PREFERRED EMBODIMENTS

Figure 5C:
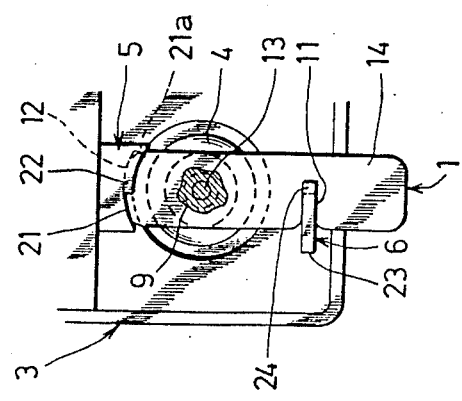
FIG. 5 (A), (B) and (C) are schematic views illustrating the operation of mounting a diffusion-limiting membrane with the use of the apparatus for mounting a diffusion-limiting membrane for a sensor in accordance with the present invention.

FIG. 3 is a perspective view of an example of a diffusion-limiting membrane holding plate used in the apparatus for mounting a diffusion-limiting membrane for a sensor in accordance with the present invention, while FIG. 4 is a longitudinal section view thereof.

In FIG. 3, the holding plate has a relatively resilient thin plate 1 substantially in the form of a rectangle which has resistance against a target solution to be measured. The resilient thin plate 1 has a square engagement cutaway portion 11 at the center of one longer side thereof. One shorter side 12 is arcuate. The resilient thin plate 1 has a circular opening 13 of which center is positioned at the center of a circle including the arc. A diffusion-limiting membrane 2 is attached to the underside of the resilient thin plate 1 with adhesives or by other suitable means, such that the opening 13 is covered by this membrane 2. That portion of the resilient thin plate 1 which is located in the vicinity of the other shorter side, serves as a holding portion 14.

FIG. 1 is a plan view of main portions of an apparatus for mounting a diffusion-limiting membrane for a sensor in accordance with a first embodiment of the present invention, while FIG. 2 is a longitudinal section view thereof.

A sensor body 3 includes an enzyme electrode unit 4 at a predetermined position thereof such that there projects upward the side of the enzyme electrode unit 4 on which an enzyme-immobilized membrane having a physiologic active substance immobilized therein or thereon is to be mounted. The sensor body 3 also has positioning portions 5 and 6 opposite to each other with respect to the enzyme electrode unit 4.

More specifically, the positioning portion 5 has an engagement concave 21 of which inner part has an arcuate surface having the same radius of curvature as that of the shorter side 12 of the resilient thin plate 1. The positioning portion 5 also has a projection 22 which constitutes an upper regulating projection of the engagement concave 21. The engagement concave 21 is provided at a predetermined position in the vicinity of the end thereof with a rotation preventing portion 21a for preventing the rotation of the resilient thin plate 1. The projection 22 may have a wide width covering the entire width of the engagement concave 21, or may have a width narrower than the entire width of the engagement concave 21. The positioning portion 6 has a standing portion 23 having a width substantially equal to the width of the engagement concave portion 11, and an upper regulating projection 24 extending in one direction from the upper portion of the standing portion 23. The enzyme electrode unit 4 has a substantially arcuate surface. The standing portion 23 may have a square section, or preferably has a tapering section to facilitate the engagement thereof with the engagement cutaway portion 11.

A diffusion-limiting membrane may be mounted on the sensor body 3 having the arrangement above-mentioned in the following manner.

Figure 5B:
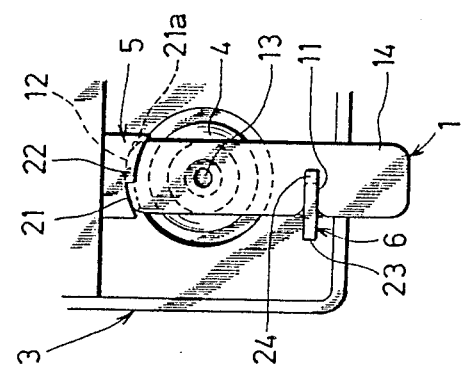
Figure 5A:
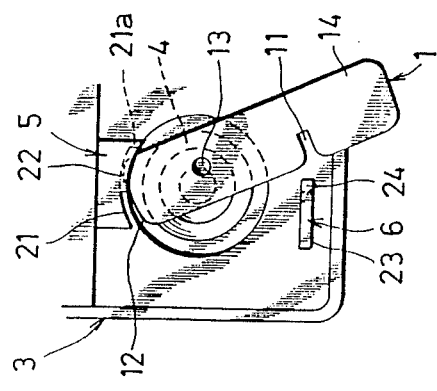

With the diffusion-limiting membrane 2 positioned at the underside of the resilient thin plate 1, the shorter side 12 of the resilient thin plate 1 is inserted into the engagement concave 21 (At this time, the center of the opening 13 is positionally shifted from the center of the enzyme electrode unit 4 as shown in FIG. 5(A)). With the resilient thin plate 1 resiliently bent such that the diffusion-limiting membrane 2 is stuck to the surface of the enzyme electrode unit 4, the resilient thin plate 1 is rotated in such direction that the engagement cutaway portion 11 is engaged with the positioning portion 6. The upper regulating projection 24 of the positioning portion 6 prevents the resilient thin plate 1 from being restored to a non-bent state (See FIG. 5 (B)). This permits the diffusion-limiting membrane 2 to be stuck to the enzyme electrode unit 4 while being held at an accurate relative position with respect thereto.

Then, a target solution to be measured 9 is dropped on the resilient thin plate 1 at its predetermined area including the opening 13, as shown in FIG. 5 (C). The target solution 9 is guided to the diffusion-limiting membrane 2 through the opening 13. The solution then reaches to the enzyme electrode unit 4 with a target substance therein limited in diffusion by the diffusion-limiting membrane 2 to lower the concentration of the target substance to some degree. Accordingly, even though the concentration of a target substance to be measured in a target solution is originally high, a concentration measurement of the target solution can be made with the concentration of the target substance considerably lowered.

After the measurement has been finished, the resilient thin plate 1 may be easily removed by reversing the mounting operations mentioned earlier. More specifically, when a measurement has been made for a target solution to be measured containing interfering substances having particle-diameters larger than that of a target substance to be measured in the target solution, the next measurement may be influenced by the interfering substances to produce an error in measured data if the next measurement is made with the diffusion-limiting membrane holding plate used for the previous measurement (even though a refresh operation has been made for removing an energization interfering membrane produced on the enzyme electrode unit 4). In such case, the diffusion-limiting membrane 2 may be removed together with the resilient thin plate 1 and replaced with a new diffusion-limiting membrane 2 to which no influence is being exerted by interfering substances.

In the diffusion-limiting membrane holding plate in FIG. 3, the resilient thin plate 1 may have a surface having hydrophobic property while only the wall of the opening 13 is hydrophilic. Such arrangement assures a smooth guidance of the target solution to be measured 9 which has been dropped, to the opening 13.

As apparent from the foregoing, the replaceable diffusion-limiting membrane 2 is attached to the resilient thin plate 1. Accordingly, the diffusion-limiting membrane 2 may be accurately positioned with respect to the enzyme electrode unit 4 and uniformly pressed thereto by merely engaging the resilient thin plate 1 with the engagement concave 21 and the positioning portion 6. Further, the diffusion-limiting membrane holding plate is generally thin. Accordingly, even though a number of diffusion-limiting membrane holding plates are stacked, the entire bulkiness can be lowered. This enables a number of the diffusion-limiting membrane holding plates to be preserved and/or transported in a small space.

Figure 6:
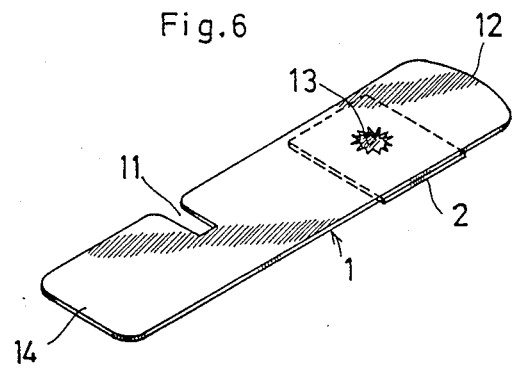
FIG. 6 to FIG. 8 are perspective views of other examples of the diffusion-limiting membrane holding plate, respectively.

FIG. 6 is a perspective view of another example of the diffusion-limiting membrane holding plate. This example is the same as the example in FIGS. 3 and 4, except that the periphery of the opening 13 in FIG. 6 has a number of convexo-concave portions.

In this example, even though the wall of the opening 13 has no high hydrophilic nature, a target solution to be measured 9 can be smoothly guided to the opening 13. However, it is a matter of course that the wall of the opening 13 having hydrophilic nature may assure a more smooth guidance of the target solution to the opening 13.

Figure 7:
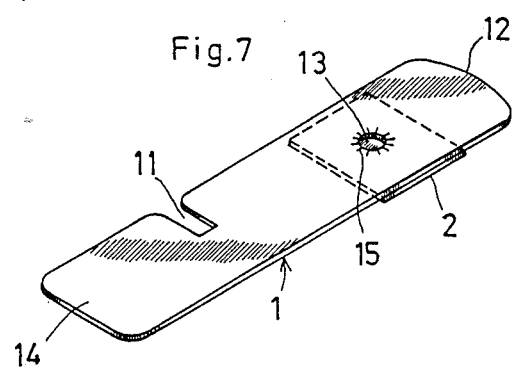

FIG. 7 is a perspective view of still another example of the diffusion-limiting membrane holding plate.

This example is the same as the example in FIGS. 3 and 4, except that a plurality of grooves 15 are formed at the periphery of the opening 13, the grooves 15 radially extending around the opening 13.

In this example also, the grooves 15 assure a smooth guidance of a target solution to be measured 9 to the opening 13.

Figure 8:
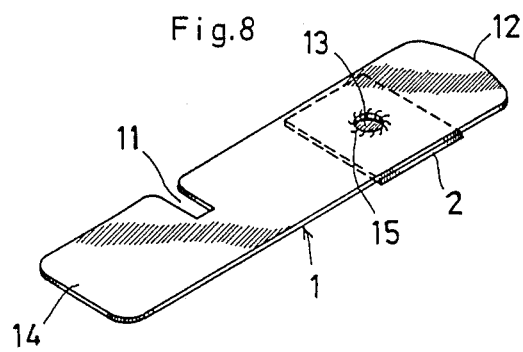

Each of the grooves 15 is not required to be linear as shown in FIG. 7, but may be spiral as shown in FIG. 8.

Figure 9:
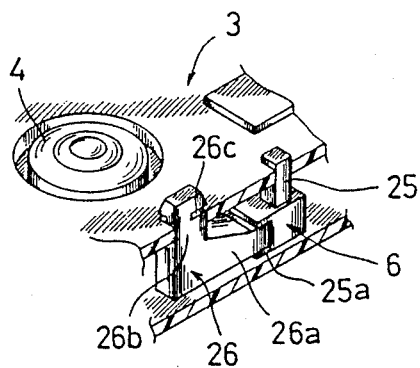
FIG. 9 is a perspective view of main portions of an apparatus for mounting a diffusion-limiting membrane for a sensor in accordance with a second embodiment of the present invention.

FIG. 9 is a perspective view of an apparatus for mounting a diffusion-limiting membrane for a sensor in accordance with a second embodiment of the present invention.

The second embodiment is the same as the first embodiment in FIGS. 1 and 2, except that a positioning portion 6 is vertically movable in FIG. 9.

More specifically, the positioning portion 6 has a status selecting member 25 mounted on a sensor body 3 and adapted to take a projecting position and a pushed position each time pressing force is directly or indirectly applied to the member 25, and a follower member 26 adapted to be vertically moved in association with the operation of the status selecting member 25.

A spring (not shown) normally biases the status selecting member 25 in the direction opposite to that of the pressing force above-mentioned. The status selecting member 25 has a known arrangement including a cam mechanism (not shown) or the like arranged such that the status where the member 25 is held as pushed, and the status where the member 25 pushed status is released, are alternately selected each time the pressing force is applied. The status selecting member 25 is provided at a predetermined position thereof with a connection piece 25a for connecting the follower member 26 to the member 25.

The follower member 26 has an arm 26a which has one end connected to the connection piece 25a and the other end of a standing piece 26b integral with the arm 26a. The standing piece 26b is provided in a predetermined position thereof with a groove 26c into which the resilient thin plate 1 is to be fittingly inserted. The remaining portion of the standing piece 26b which is contiguous to the groove 26c, has a predetermined width of which the widest portion is not greater than the width of the engagement cutaway portion 11 of the resilient thin plate 1.

According to this second embodiment, a pressing force may be exerted to the status selecting member 25 with the resilient thin plate 1 engaged with one positioning portion 5 and the follower member 26. This causes the follower member 26 to be lowered. With such lowered status maintained, the resilient thin plate 1 is resiliently bent to cause the diffusion-limiting membrane 2 to be stuck to the enzyme electrode unit 4.

When the diffusion-limiting membrane 2 is to be removed, a pressing force may be exerted to the status selecting member 25 to release the status where the follower member 26 is held as lowered. This causes the diffusion-limiting membrane 2 to be separated from the enzyme electrode unit 4. Thus, the diffusion-limiting membrane 2 may be easily removed.

As apparent from the foregoing, when the diffusion-limiting membrane 2 is mounted on or removed from the enzyme electrode unit 4, the diffusion-limiting membrane 2 merely comes in contact with or separates from the surface of the enzyme electrode unit 4. This means that both membrane and electrode unit surface are not slidingly rubbed with each other. This prevents the enzyme-immobilized membrane attached to the surface of the enzyme electrode unit 4 from being deteriorated in enzyme activity due to falling-off of the enzyme from the enzyme-immobilized membrane.

In the second embodiment in FIG. 9, the status selecting member 25 is located at a position different from the position at which the standing piece 26b is located. However, if both member 25 and standing piece 26b may be located at the same position, the arm 26a may be omitted and the status selecting member 25 may be formed integrally with the follower member 26.

Figure 10:
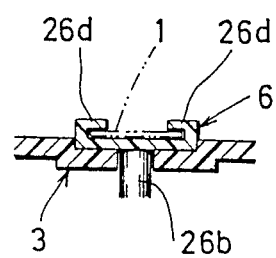
FIG. 10 and FIGS. 11 A and B are perspective views of main portions of an apparatus for mounting a diffusion-limiting membrane for a sensor in accordance with third and fourth embodiments of the present invention, respectively.

The arrangement of the standing piece 26b is not limited to that shown in FIG. 9. For example, as shown in FIG. 10 holding pieces 26d may be formed for slidably holding both longer sides of a resilient thin plate 1 having no engagement cutaway portion 11. This arrangement enables the resilient thin plate 1 to be set by sliding the same.

Figure 11A:
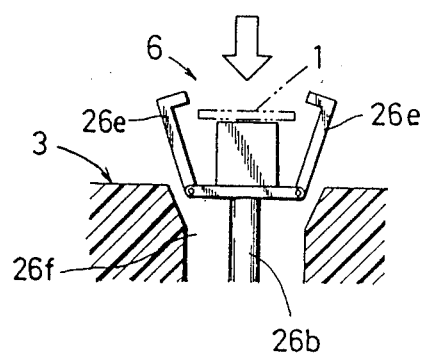
Figure 11B:
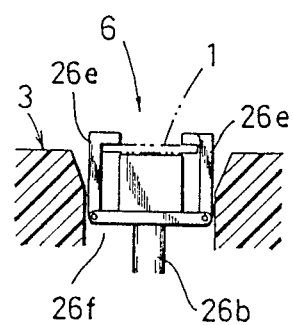

Alternatively, as shown in FIG. 11 holding pieces 26e for slidably holding both longer sides of the resilient thin plate 1 may be formed such that the holding pieces 26e are movable in both directions toward and away from each other. Disposed in mid-portion of the moving passage of the holding pieces 26e is a forcibly rotating piece 26f for forcibly rotating the holding pieces 26e in a direction toward each other. By the forcibly rotating piece 26f, the holding pieces 26e are rotated in a direction toward each other, while being lowered. This enables the resilient thin plate 1 to be horizontally positioned, and also enables the status thus positioned to be maintained (See FIG. 11 (B)).

Figure 12:
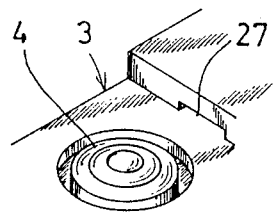
FIG. 12 is a schematic perspective view of another example of main portions of the apparatus for mounting a diffusion-limiting membrane for a sensor in accordance with the present invention.

The arrangement of the shorter-side engagement portions is not limited to that having the engagement concave 21 and the projection 22. Such shorter-side engagement portion may be formed by a slit 27 only as shown in FIG. 12. With the use of the slit 27, the resilient thin plate 1 may be easily mounted and removed as done with the arrangement in FIG. 1.

The arrangement of the resilient thin plate 1 is not limited to those shown in FIGS. 3 to 8. For example, the holding-portion side of the resilient thin plate 1 may be turned in the form of a mountain to enhance the strength thereof.

Figure 13A:
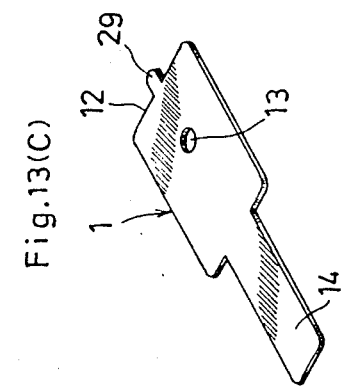
FIGS. 13 A, B and C and FIGS. 14 A and B are perspective views of still other examples of the diffusion-limiting membrane holding plate, respectively.
Figure 13B:
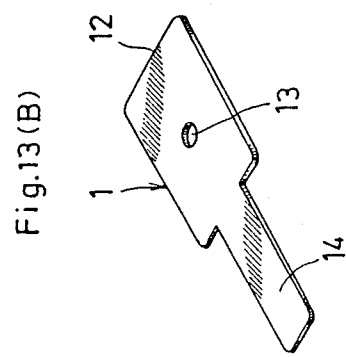
Figure 13C:
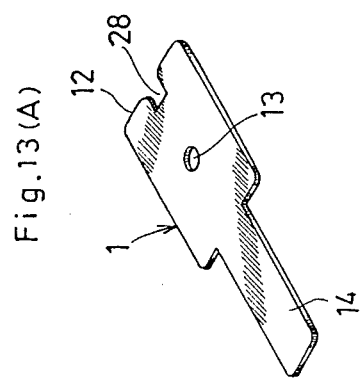

As shown in FIG. 13 (A), (B) and (C), the resilient thin plate 1 has a narrower holding-portion side and a wider end side 12 which is provided with a positioning notched concave 28 (See FIG. 13 (A)) or which is provided with a positioning projection 29 (See FIG. 13 (C)).

Figure 14A:
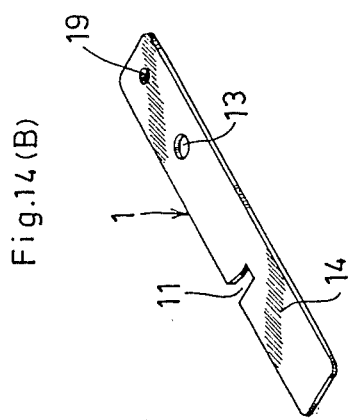
Figure 14B:
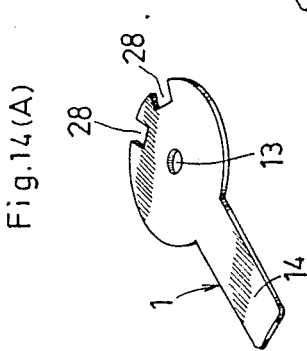

Further, as shown in FIG. 14 (A), the resilient thin plate 1 may have, as a wider side, a circular portion which is provided at a predetermined position of the periphery thereof with at least one positioning notched concave 28. As shown in FIG. 14 (B), the resilient thin plate 1 may have a positioning hole 19 at a predetermined position in the vicinity of one end side thereof.

Further, one shorter side and a predetermined portion of one longer side of the resilient thin plate 1 of which the ratio of the longer side to the shorter side is considerable or not so considerable, may be used, as they are, as positioning engagement portions. It is noted that such arrangement is not shown in the attached drawings.

When the resilient thin plate 1 having the arrangement shown in FIG. 13 or 14, is used, the engagement portion 5 may have a projection which is adapted to be engaged with the notched concave or hole, or the engagement portion 5 may have a concave which is adapted to be engaged with the projection, whereby accurate positioning is assured.

As to mounting the resilient thin plate 1 at its one end side, the resilient thin plate 1 may be inserted in an arbitrary direction, or horizontally slid along a guide groove or the like when the sensor has such guide groove or the like. Alternatively, the resilient thin plate 1 may be slid downward along at least one guide projection when the sensor has such guide projection.

Figure 15:
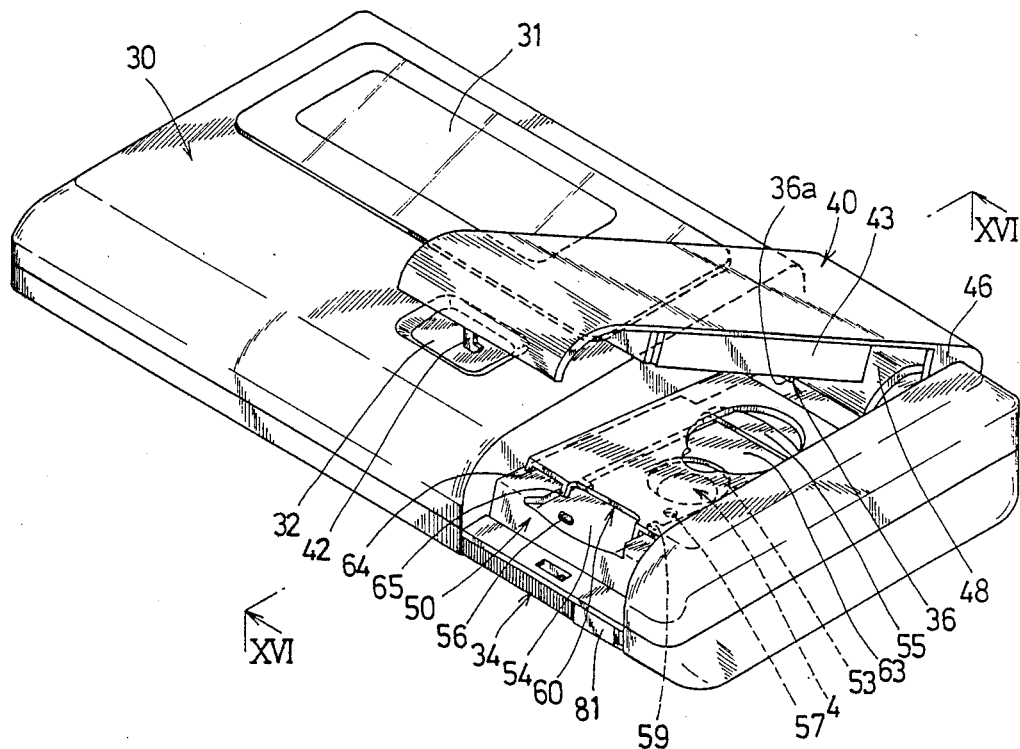
FIG. 15 is a schematic perspective view of a blood sugar level measuring apparatus incorporating the apparatus for mounting a diffusion-limiting membrane for a sensor in accordance with the present invention.
Figure 16:
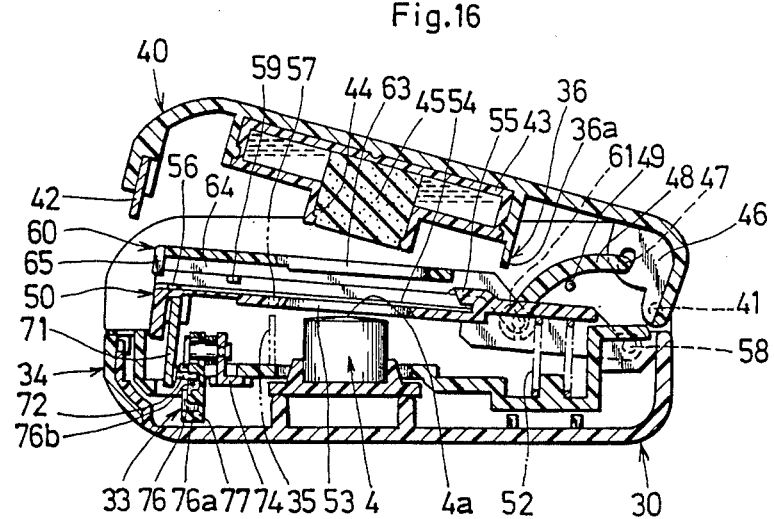
FIG. 16 is a section view taken along the line XVI—XVI of FIG. 15.

FIG. 15 is a schematic perspective view of a blood sugar level measuring apparatus incorporating the apparatus for mounting a diffusion-limiting membrane for a sensor in accordance with the present invention, while FIG. 16 is a longitudinal section view thereof.

The apparatus in FIG. 15 has a casing 30, a display 31 at a predetermined position of the casing 30, an operation switch 32 and an openable outer cover 40. An enzyme electrode unit 4, a mounting member 50 for mounting a diffusion-limiting membrane holding plate and an inner cover 60 are disposed in predetermined positional relations with respect to the outer cover 40.

Figure 17:
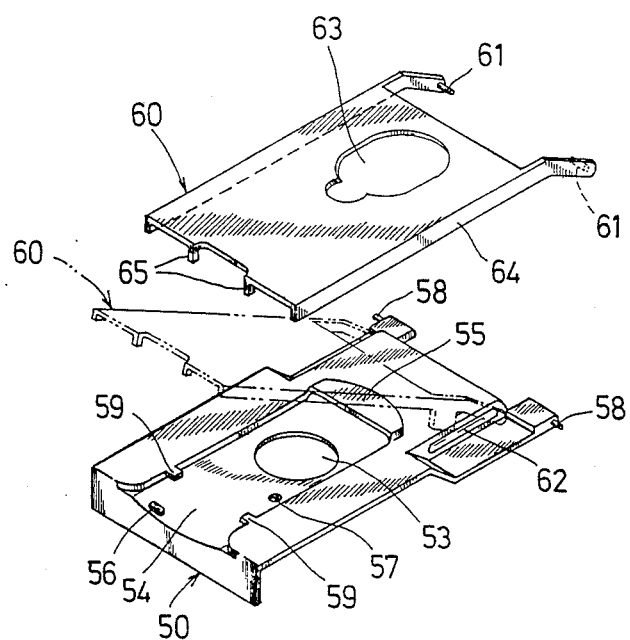
FIG. 17 is an exploded perspective view illustrating a relationship between a mounting member for mounting a diffusion-limiting membrane holding plate and an inner cover.
Figure 18:
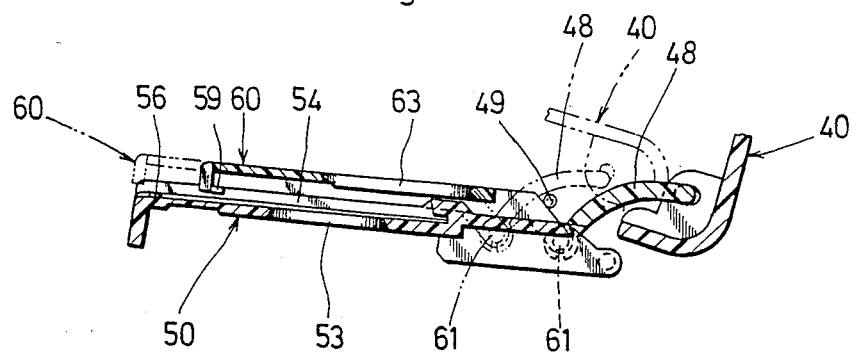
FIG. 18 is a schematic longitudinal section view of FIG. 17.

The following description will be made in more detail also with reference to FIGS. 17 and 18 showing the main portions of the apparatus in FIG. 15.

The enzyme electrode unit 4 attached to the casing 30 has base electrodes (not shown), and a GOD immobilized membrane 4a covering the base electrodes. The enzyme electrode unit 4 has an arcuate convexed surface at its top. The mounting member 50 for mounting a diffusion-limiting membrane holding plate has a through-hole 53 into which the enzyme electrode unit 4 may be inserted. The mounting member 50 is provided at a predetermined position of the top surface thereof with a housing groove 54 for housing a diffusion-limiting membrane holding plate to be discussed later. The housing groove 54 has a width equal to that of the diffusion-limiting membrane holding plate. The mounting member 50 is provided at a position slightly above the housing groove 54 with an upper flange 55 which projects toward the through-hole 53. The mounting member 50 is further provided with inner cover positioning projections 59 which project from predetermined positions of the top open sides of the housing groove 54. The housing groove 54 is provided with an engagement projection 56 and a through-hole 57 at predetermined positions thereof. The mounting member 50 is vertically rotatably connected to the casing 30 by shafts 58. A positioning mechanism 33 to be discussed later regulates the vertically rotatable range of the mounting member 50. A positioning release mechanism 36 to be also discussed later may release the status where the mounting member 50 has been moved in close to the enzyme electrode unit 4, such status having being provided by the positioning mechanism 33. A release mechanism 37 to be also discussed later may release the status where the mounting member 50 has been limited in vertically rotatable range, such status having been provided by the positioning mechanism 33. A spring 52 is disposed between the casing 30 and the mounting member 50 for normally biasing the mounting member 50 such that the same is upwardly rotated. The casing 30 is provided at a predetermined position thereof with a pulling preventive shaft 35 adapted to project upward through the through-hole 57 when the mounting member 50 is rotated downward.

As shown in more detail in FIGS. 17 and 18, the inner cover 60 has a pair of inwardly projecting portions 61 which are slidably and rotatably engaged with guide grooves 62 formed in the mounting member 50 in predetermined ranges thereof in the vicinity of the shafts 58. The inner cover 60 is also provided with a large-diameter hole 63 adapted to be opposite to the through-hole 53 when the projections 61 are slid to the positions remotest from the shafts 58. The inner cover 60 is provided with downwardly projecting portions 64 at the undersides of the ends thereof in parallel to the sliding direction of the inner cover 60. The inner cover 60 is also provided at predetermined inner positions thereof with downwardly projecting portions 65 adapted to be engaged with the inner cover positioning projections 59.

The outer cover 40 is rotatably mounted on the casing 30 by a shaft 41 at one end thereof in the vicinity of the guide grooves 62. The outer cover 40 is provided at the other end thereof with an engagement portion 42 engaged with a slide engagement portion 34 which is provided at a predetermined position of the casing 30. The engagement of the slide engagement portion 34 with the engagement portion 42 causes the outer cover 40 to be held as closed. The outer cover 40 is provided at a predetermined position of the lower surface thereof with a wetting liquid housing tank 43 removably disposed. The wetting liquid housing tank 43 is provided with an open portion 44 adapted to be opposite to the enzyme electrode unit 4 when the outer cover 40 is closed. A sponge 45 is housed in the open portion 44. The outer cover 40 is provided at the end thereof in the vicinity of the shaft 41 with downwardly turned flanges 46. Links 48 are rotatably connected to the downwardly turned flanges 46 by shafts 47. The links 48 are engaged at the tips thereof with inwardly projecting portions 61. The casing 30 is provided at predetermined positions thereof with inwardly projecting portions 49. These projections 49 are adapted to be engaged with the inner cover 60 at predetermined positions thereof in the vicinity of the base of the inner cover 60 which is moved in association with the operation of opening the outer cover 40. Such engagement causes the inner cover 60 to be pressed to the mounting member 50.

Figure 23:
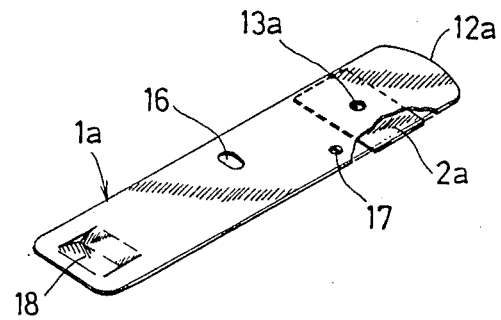
FIG. 23 is a perspective view of yet another example of the diffusion-limiting membrane holding plate to be mounted on the apparatus for mounting a diffusion-limiting membrane for a sensor shown in FIGS. 15 and 16.
Figure 24A:
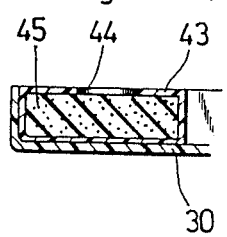
FIG. 24 (A) to (C) and (E) to (H) are center longitudinal section views of a wetting liquid housing tank with a sponge housed therein, respectively.
Figure 24B:
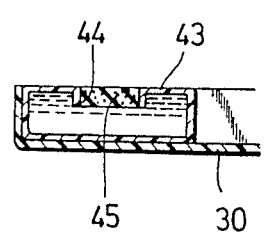
Figure 24C:
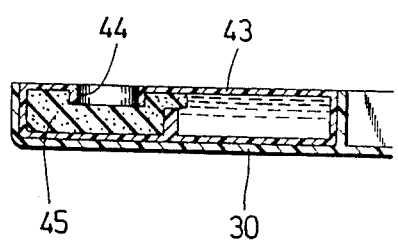
Figure 24D:
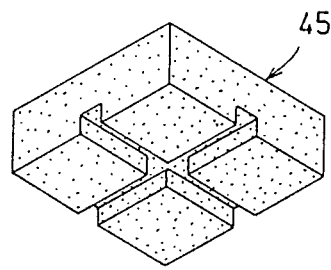
Figure 24E:
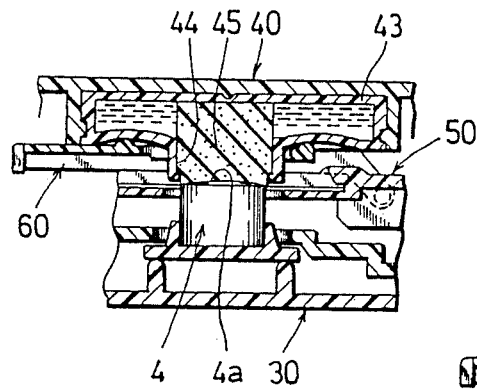
Figure 24F:
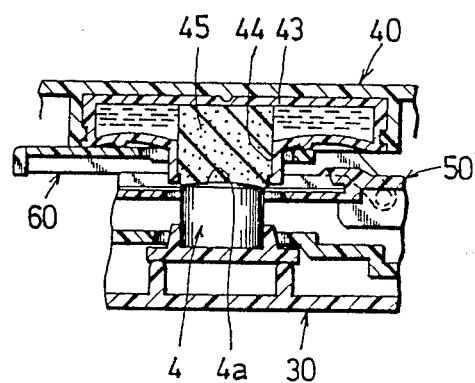
Figure 24G:
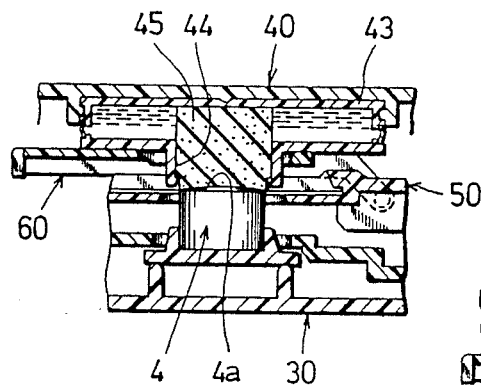
Figure 24H:
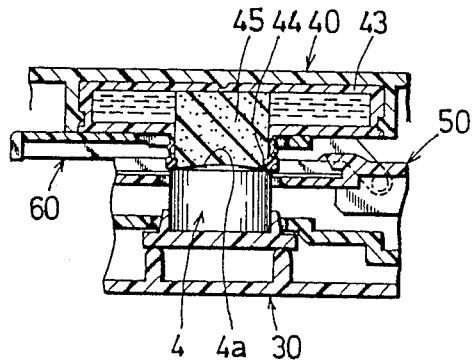

As shown in FIG. 23, the diffusion-limiting membrane holding plate above-mentioned has a long-size resilient thin plate 1a having one shorter arcuate side 12a. The resilient thin plate 1a is provided in a predetermined position thereof with an opening 13a which is adapted to be opposite to the enzyme electrode unit 4 when the diffusion-limiting membrane holding plate is mounted on the apparatus of the present invention. The resilient thin plate 1a has openings 16 and 17 adapted to be opposite to the engagement projection 56 and the hole 57, respectively. The opening 13a is covered by a diffusion-limiting membrane 2a. The resilient thin plate 1a is further provided with a downwardly projecting portion 18 in the vicinity of the other shorter side thereof. This projecting portion 18 facilitates to hold the diffusion-limiting membrane holding plate regardless of a place on which the diffusion-limiting membrane holding plate is put.

Figure 19:
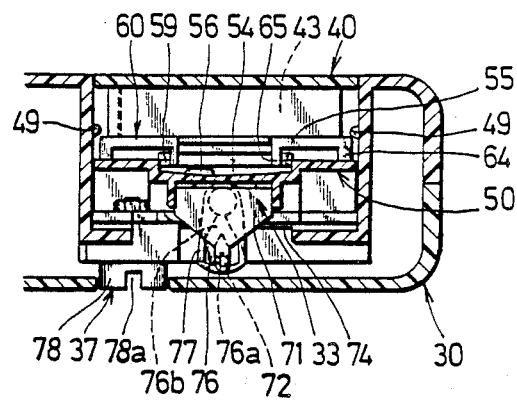
FIG. 19 is a longitudinal section view of main portions of a positioning mechanism.
Figure 20:
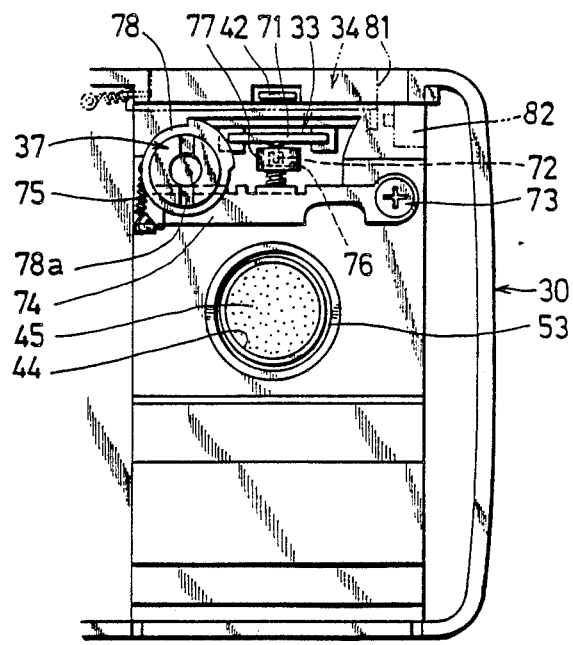
FIG. 20 is a bottom view of FIG. 15 with portions of a casing broken away.

FIG. 19 is a longitudinal section view of main portions of the positioning mechanism. FIG. 20 is a bottom view of FIG. 15 with portions of the casing broken away.

As shown in detail in FIGS. 17 and 18, the mounting member 50 for mounting a diffusion-limiting membrane holding plate is provided at the underside of the tip thereof with a flange 71. The flange 71 is provided at a predetermined position of the lower portion thereof with an engagement shaft 72 which extends toward the shafts 58. The casing 30 is provided at a predetermined position thereof with a lever 74 which is horizontally rotatable around a shaft 73. A spring 75 is disposed for biasing the lever 74 such that the same is normally rotated in a direction away from the shafts 58. The lever 74 is provided in the center thereof with a stopper 77 including an endless groove 76 engaged with the engagement shaft 72, which is swingable in association with the vertical movement of the engagement shaft 72. The groove 76 is provided with a pair of upwardly turned concaves 76a and 76b which are aligned with the swing center of the stopper 77. The concaves 76a and 76b are arranged such that, when the engagement shaft 72 is engaged with either of the concaves 76a and 76b, the mounting member 50 is rotated up to the upper or lower rotation limit position.

A rotation member 78 serving as the release mechanism 37 is exposed to the outside from the lower surface of the casing 30. The rotation member 78 may take a position permitting the lever 74 to be rotated by the spring 75, i.e., a state where the engagement of the engagement shaft 72 with the groove 76 is held, and a position preventing the lever 74 from being rotated against the spring 75, i.e., a state where the engagement shaft 72 is disengaged from the groove 76.

The positioning release mechanism 36 above-mentioned is constituted by a pushing shaft 36a which is projectingly formed at a predetermined position of the lower surface of the outer cover 40. When the outer cover 40 is closed, the pushing shaft 36a is adapted to forcibly rotate the mounting member 50 downward. Such rotation causes the engagement shaft 72 to be disengaged from the upwardly turned concave 76a. The rotation member 78 is provided with an engagement groove 78a at that portion of the casing 30 which is exposed to the outside. This grooves 78a may be useful for rotating the rotation member 78 with a dedicated operation means, a coin or the like. The casing 30 is provided with a slidable lock member 81 for holding the outer cover 40 as closed. The casing 30 is also provided with a limit switch 82 adapted to be turned ON when the lock member 81 is slid in a non-lock direction. Thus, merely sliding the lock member 81 enables the limit switch 82 to be automatically operated.

The following description will discuss the operation of the blood sugar level measuring apparatus having the arrangement above-mentioned.

Figure 21A:
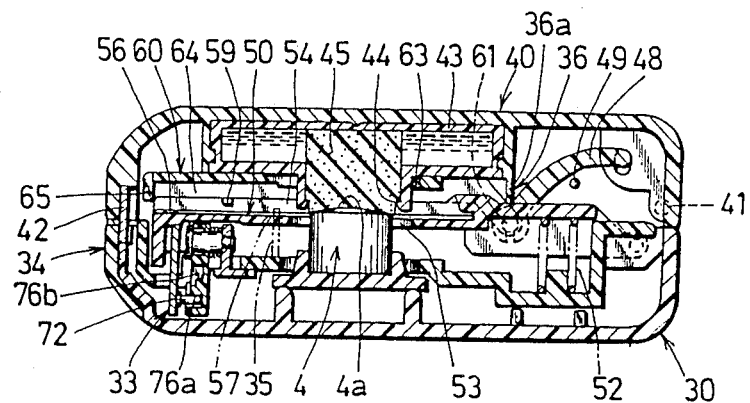
FIG. 21 (A), (B) and (C) are views illustrating the operation of mounting a diffusion-limiting membrane.
Figure 21B:
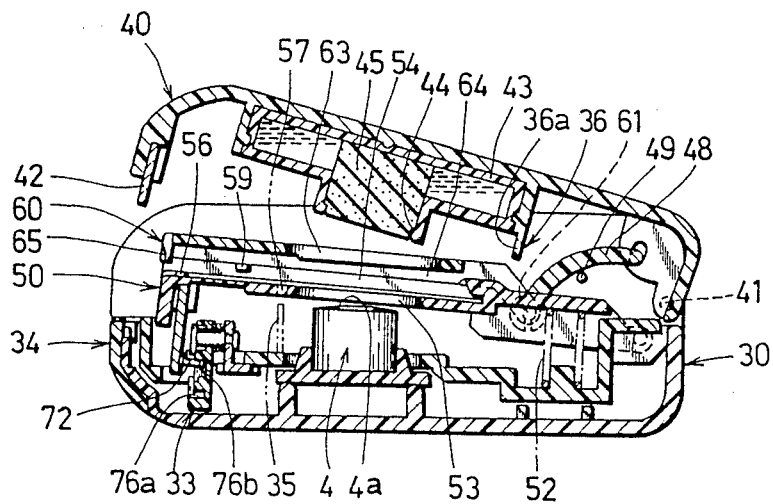
Figure 21C:
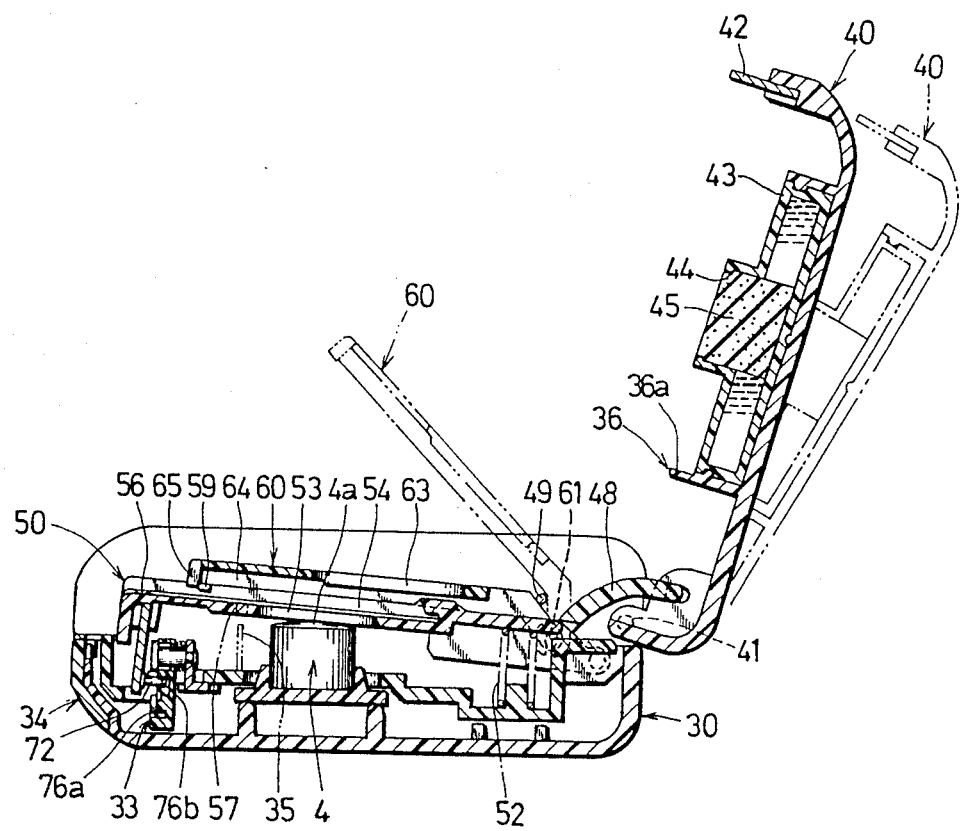

When no measurement of a blood sugar level is to be made, it is enough to maintain the outer cover 40 as closed. That is, the engagement portion 42 is engaged with the slide engagement portion 34 to hold the outer cover 40 as closed, and the sponge 45 housed in the open portion 44 of the wetting liquid housing tank 43 comes in contact with the enzyme electrode unit 4 to maintain the GOD immobilized membrane 4a wet. This enables the GOD immobilized membrane 4a to be kept with the activity thereof not deteriorated (See FIG. 21 (A)).

In such state, the engagement shaft 72 disposed on the mounting member 50 is downwardly moved against the spring 52, and the downward moving distance is regulated by the pushing shaft 36a serving as the positioning release mechanism 36. This prevents the engagement shaft 72 from being held as engaged with the upwardly turned concave 76a. Accordingly, when the pressing force applied by the pushing shaft 36a is released, the engagement shaft 72 is continuously held so as to be automatically movable in such direction that the engagement shaft 72 is engaged with the other upwardly turned concave 76b.

When the outer cover 40 is closed, the links 48 exert force to the inner cover 60 in a direction substantially equal to the sliding direction of the inner cover 60. This assures a smooth sliding of the inner cover 60.

When a measurement of blood sugar level is to be made, the slide engagement portion 34 may be slid to release the closing of the outer cover 40. By the spring 52, the engagement shaft 72 is upwardly moved together with the mounting member 50 and positioned with the engagement shaft 72 engaged with the upwardly turned concave 76b. Then, the diffusion-limiting membrane holding plate on the opening 13a of which blood has been dropped, is mounted on the mounting member 50. Thereafter, the mounting member 50 may be rotated downward against the spring 52, causing the GOD immobilized membrane 4a and the diffusion-limiting membrane 2a to be stuck to each other. When the operation switch 32 has been previously operated, an electric signal is taken out from the enzyme electrode unit 4. Based on the electric signal thus taken out, a necessary processing is carried out to visually display a blood sugar level on the display 31.

More specifically, at the final stage of the operation of closing the outer cover 40, the pushing shaft 36a serving as the positioning release mechanism 36 forcibly rotates the mounting member 50 downward to disengage the engagement shaft 72 from the upwardly turned concave 76a. Accordingly, when the outer cover 40 is opened for the next measurement, the spring-load of the spring 52 causes the mounting member 50, the inner cover 60 and the outer cover 40 to be automatically rotated upward to some extent (See FIG. 21 (B)). Accordingly, the outer cover 40 may be freely rotated thereafter. When the outer cover 40 is rotated upward, the links 48 are moved toward the shaft 41 with the rotation thereof considerably restrained, since the links 48 are engaged at the tips thereof with the inwardly projecting portions 61. As the result, the inner cover 60 is also moved toward the shaft 41 (See FIG. 21 (C)). Since a pair of inwardly projecting portions 61 are merely engaged with the guide grooves 62, there is a possibility of the inner cover 60 being vertically rotated if as it is. However, when the inner cover 60 is engaged with the inwardly projecting portions 49, a downward directional force is applied to the inner cover 60. Accordingly, the downwardly projecting portions 64 are pressed to the upper surface of the mounting member 50 and the downwardly projecting portions 65 are engaged with the inner cover positioning projections 59.

Then, the diffusion-limiting membrane holding plate on which blood has been dropped, is inserted into the housing groove 54. The diffusion-limiting membrane holding plate is positioned such that the opening 16 of the holding plate is engaged with the engagement projection 56. A downward directional force is then exerted to the inner cover 60, causing the same to be downwardly rotated together with the mounting member 50. The engagement shaft 72 is then engaged with the upwardly turned lower concave 76a. Thus, the mounting member 50 is held as downwardly rotated, enabling the diffusion-limiting membrane 2a of the holding plate to be stuck to the GOD immobilized membrane 4a of the enzyme electrode unit 4. The pulling preventive shaft 35 projecting through the hole 57 is engaged with the opening 17. This prevents not only the diffusion-limiting membrane holding plate from being forcibly pulled out, but also the GOD immobilized membrane 4a from being deteriorated due to friction. Also, when the diffusion-limiting membrane holding plate is mounted, the GOD immobilized membrane 4a may be prevented from being deteriorated due to friction.

Accordingly, when the operation switch 32 has been already operated, a measurement of blood sugar level may be made and the measured data may be visually displayed on the display 31.

After the measurement has been finished, the engagement shaft 72 may be disengaged from the upwardly turned lower concave 76a by exerting a downward directional force to the inner cover 60. When the downward directional force is released, the spring-load of the spring 52 causes the inner cover 60 and the mounting member 50 to be upwardly rotated. This releases the adhesion of the diffusion-limiting membrane 2a to the GOD immobilized membrane 4a, and also disengages the pulling preventive shaft 35 from the opening 17.

Accordingly, the diffusion-limiting membrane holding plate may be pulled out with no friction force applied to the GOD immobilized membrane 4a.

When carrying out the next measurement of blood sugar level, blood may be dropped on a new diffusion-limiting membrane holding plate and a series of operations above-mentioned may be carried out.

If the housing groove 54 is contaminated after a plurality of of measurements have been made, the outer cover 40, may be rotated by an angle exceeding a normal angle range, thereby to apply a great rotating force to the inner cover 60 through the links 48. Consequently, the inner cover 60 is upwardly rotated over the inwardly projecting portions 49 such that the mounting member 50 is perfectly opened at its top surface (See the state shown by the long and two short dashes lines in FIG. 21 (C)).

Accordingly, the contaminated housing groove 54 may be easily cleaned without disassembling the blood sugar level measuring apparatus.

However, even though the outer cover 40 has been opened in a normal angle range only, an upwardly rotating force greater than a predetermined amount may be exerted to the inner cover 60. Thus, the inner cover 60 may be sufficiently rotated upwardly over the inwardly projecting portions 49 such that the mounting member 50 is opened at its top surface. Accordingly, the contaminated housing groove 54 may be easily cleaned without disassembling the blood sugar level measuring apparatus.

If the GOD immobilized membrane 4a is deteriorated in activity after a plurality of measurements have been made, the rotation member 78 may be rotated with a dedicated operating means, a coin or the like. The lever 74 may be rotated against the spring 75 to disengage the engagement shaft 72 from the groove 76 of the stopper 77. This enables the mounting member 50 to be upwardly rotated by the spring 52 without no restrictions imposed thereon.

In such state or in a state where the mounting member 50 is further rotated upwardly by a manual operation, the enzyme electrode unit 4 may be taken out from the through-hole 53 and a relatively wide free space may be obtained around the enzyme electrode unit 4. This enables the GOD immobilized membrane 4a to be easily removed and mounted. In such state, it is possible to easily replace not only the GOD immobilized membrane 4a, but also other membrane (not shown) or the electrode unit itself.

Figure 22A:
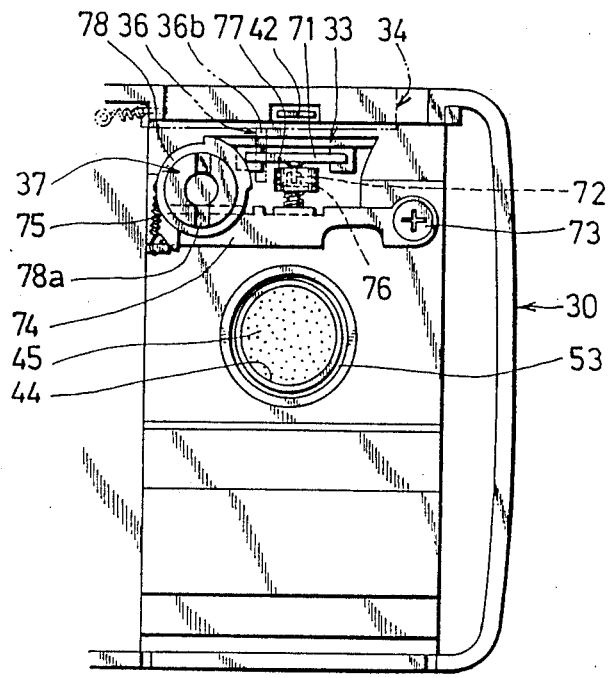
FIG. 22 (A) is a bottom view of main portions of a blood sugar level measuring apparatus incorporating another example of a positioning release mechanism.
Figure 22B:
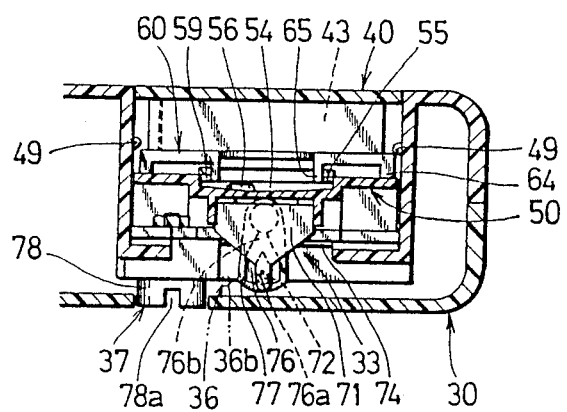

Instead of the positioning release mechanism 36 constituted by the pushing shaft 36a, there may be used a positioning release mechanism 36 having a lever 36b integral with the slide engagement portion 34 as shown in FIG. 22.

More specifically, when the slide engagement portion 34 is slid in one direction, the lever 36b is adapted to be engaged with the lateral side of the stopper 77 to forcibly swing the stopper 77. This causes the engagement shaft 72 to be disengaged from the upwardly turned concave 76a.

In such case, when the slide engagement portion 34 is operated to open the outer cover 40, the lever 36b is engaged with the lateral side of the stopper 77 to swing the same forcibly. This securely disengages the engagement shaft 72 from the upwardly turned concave 76a.

As apparent from the foregoing, with the mounting member 50 upwardly rotated, the diffusion-limiting membrane holding plate may be mounted and removed without sliding friction thereof with the GOD immobilized membrane 4a. At the time of measurement, the mounting member 50 is downwardly rotated to stick the diffusion-limiting membrane 2a to the GOD immobilized membrane 4a. Thus, a good measurement of blood sugar level may be assured. In particular, since the positioning release mechanism 36 is disposed, opening the outer cover 40 for measurement of blood sugar level causes the mounting member 50 to be upwardly rotated. In such state, the diffusion-limiting membrane holding plate may be mounted.

Further, the pulling preventive shaft 35 projects through the hole 57 and is engaged with the opening 17 in the diffusion-limiting membrane holding plate. This prevents the diffusion-limiting membrane holding plate from being mounted and removed in a state involving the likelihood that the diffusion-limiting membrane holding plate is slidingly rubbed with the GOD immobilized membrane 4a.

Further, the release mechanism 37 may release the rotatable range limiting status provided by the positioning mechanism 33. This enables the enzyme electrode unit 4 to be greatly separated from the mounting member 50. In such state, the GOD immobilized membrane 4a or the like may be easily replaced.

Further, in a state where the diffusion-limiting membrane holding plate is mounted on the mounting member 50, the large-diameter hole 63 is positionally shifted with respect to the enzyme electrode unit 4 due to the sliding of the inner cover 60. Therefore, it is substantially impossible for the operator to touch the enzyme electrode unit 4 through the large-diameter hole 63. This securely prevents the operator from carelessly touching the blood dropped on the diffusion-limiting membrane holding plate, at a time when the operator is required to concentrate his attention on the operation of pushing the inner cover 60 or the operation switch 32. Of course, when the diffusion-limiting membrane holding plate is mounted or removed, or when blood is dropped on the diffusion-limiting membrane holding plate, there is the likelihood that the operator touches the blood, since the blood is exposed. However, the operator is not required to carry out another operation while carrying out such operation. Accordingly, there is little scope left him for admission of carelessness.

When no measurement of blood sugar level is to be made, the sponge 45 housed in the open portion 44 in the wetting liquid housing tank 43 comes in contact with the enzyme electrode unit 4 to maintain the GOD immobilized membrane 4a wet. This enables the GOD immobilized membrane 4a to be held without deterioration of the activity thereof.

As shown in FIG. 24 (A), the sponge 45 may be housed in the wetting liquid housing tank 43 in its entirety. As shown in FIG. 24 (B), the sponge 45 may have a thickness substantially equal to the depth of the open portion 44. As shown in FIG. 24 (C), the sponge housing portion may be partitioned with a parting member having a low height. As shown in FIG. 24 (D), the sponge 45 may be provided at the back side thereof with grooves for improving the flowability of the wetting liquid. As shown in FIG. 24 (E) and (F), the wetting liquid housing tank 43 may be resilient, or as shown in FIG. 24 (G) and (H), the wetting liquid housing tank 43 may be provided at the main body or opening thereof with bellows to reduce the inner volume thereof at a time when the outer cover 40 is closed. Such arrangement may improve the flowability of the wetting liquid contained in the sponge 45.

Figure 25:
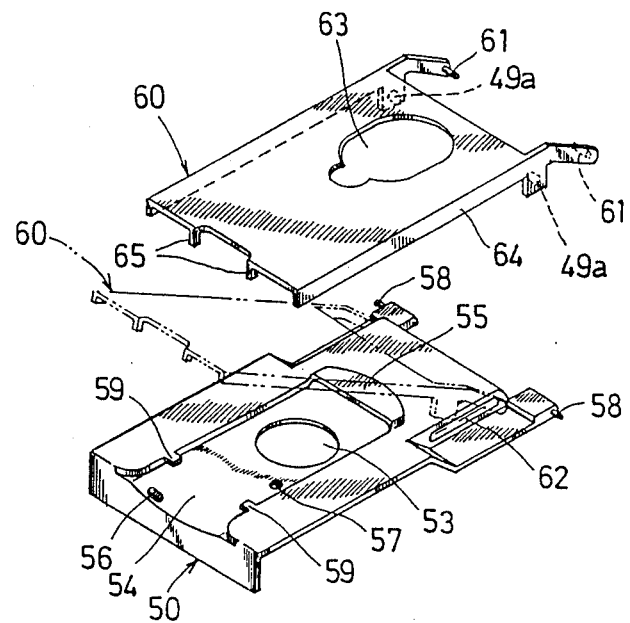
FIG. 25 is an exploded perspective view of another example of the mounting member for mounting a diffusion-limiting membrane holding plate and the inner cover.
Figure 26:
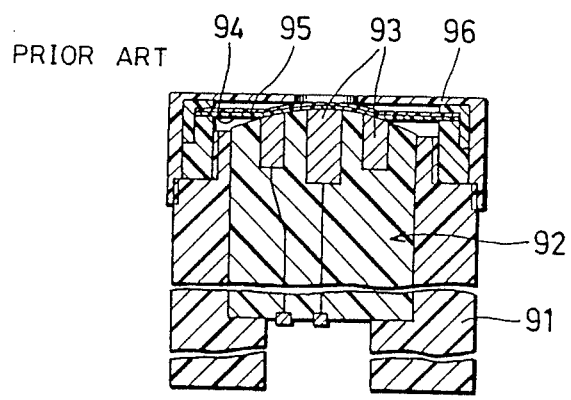
FIG. 26 is a schematic longitudinal section view of main portions of a conventional apparatus for mounting a diffusion-limiting membrane for a sensor.

FIG. 25 is an exploded perspective view of another examples of the mounting member 50 and the inner cover 60.

This example is the same as the example shown in FIGS. 15 and 17, except that the inner cover 60 in FIG. 25 does not have the inwardly projecting portions 49, but is provided at predetermined positions thereof with inwardly projecting portions 49a engaged with the guide grooves 62 together with the inwardly projecting portions 61. The engagement of the inwardly projecting portions 49a with the guide grooves 62 may be easily released by applying a rotating force exceeding a predetermined amount, to the inner cover 60.

In the example in FIG. 25, while both inwardly projecting projections 49a and 61 are engaged with the guide grooves 62, the inner cover 60 may be slid only in parallel to the mounting member 50.

When the outer cover 40 is opened by an angle exceeding a normal angle range to apply a great upwardly rotating force to the inner cover 60 through the links 48, the inwardly projecting portions 49a may be disengaged from the guide grooves 62. By upwardly rotating the inner cover 60 by a considerable angle, the top of the mounting member 50 may be opened. Accordingly, the housing groove 54 for housing a diffusion-limiting membrane holding plate may be easily cleaned, if contaminated.

Alternatively, the inner cover 60 may be provided with guide grooves, while the mounting member 50 may be provided with outwardly projecting portions. Such arrangement may achieve the same effect as that obtained in the example above-mentioned.

In any of the examples above-mentioned, the inner cover 60 may be sufficiently rotated upward by applying an upwardly rotating force greater than a predetermined amount directly to the inner cover 60 instead of opening the outer cover 40 by an angle exceeding a normal angle range.

The description hereinbefore has been made for measurement of blood sugar level, but it is a matter of course that the apparatus in accordance with the present invention may be applied to an apparatus for measuring cholesterol, neutral fat, urine or the like. Further, the apparatus of the present invention may be arranged such that the mounting member 50 for mounting a diffusion-limiting membrane holding plate may be vertically moved while being horizontally held in its entirety.

What is claimed is:

1. An apparatus for mounting a diffusion-limiting membrane for a sensor comprising:
   a pair of positioning portions on a sensor having an enzyme electrode unit, said sensor also having an enzyme-immobilized membrane, said pair of positioning portions being opposite to each other with respect to said enzyme electrode unit;
   a resilient thin plate having first and second engagement means for engagement with said pair of positioning portions, said first and second engagement means being spaced further apart than said pair of positioning portions so as to cause said resilient thin plate to be resiliently bent upon engagement of said engagement means with said positioning portions;

said resilient thin plate having an opening formed therein in a position which is adapted to be opposite to said enzyme electrode unit; and said opening being covered by a diffusion-limiting membrane secured to said resilient plate.

2. An apparatus for mounting a diffusion-limiting membrane for a sensor as set forth in claim 1, wherein the pair of positioning portions are immovably attached to the sensor.

3. An apparatus for mounting a diffusion-limiting membrane for a sensor comprising:

a mounting member for mounting a diffusion-limiting membrane holding plate;

said mounting member having a first end, a second end, an upper surface, a bottom surface and a through-hole which extends through said upper and bottom surfaces and which is adapted to house an enzyme electrode unit for measuring a target solution disposed on a sensor at a predetermined position thereof, said mounting member having a groove formed therein for housing a diffusion-limiting membrane holding plate, said groove extending to said first end of said mounting member so as to form an opening in said mounting member which enables the housing plate to extend away from said groove; and said mounting member being movable in both directions toward and away from said electrode unit; and positioning means for positioning said mounting member at a first position wherein said enzyme electrode is housed within the through-hole of said mounting member and at a second position wherein said mounting member is positioned away from said enzyme electrode unit.

4. An apparatus for mounting a diffusion-limiting membrane for a sensor as set forth in claim 3, wherein the mounting member for mounting a diffusion-limiting membrane holding plate is rotatable with one end thereof serving as a fulcrum.

5. An apparatus for mounting a diffusion-limiting membrane for a sensor as set forth in claim 3, wherein the positioning member is constituted by a swing member having a guide groove engaged with an engagement shaft disposed on the mounting member for mounting a diffusion-limiting membrane holding plate, said guide groove having a pair of engagement portions aligned with the swing center of said swing member.

6. An apparatus for mounting a diffusion-limiting membrane for a sensor as set forth in claim 5, further comprising:

an openable outer cover covering the top of the mounting member for mounting a diffusion-limiting membrane holding plate; and positioning release means for releasing a state where said mounting member is positioned at the moved position in a direction toward the enzyme electrode unit, in association with the operation of closing said outer cover, said state having been provided by the said positioning means.

7. An apparatus for mounting a diffusion-limiting membrane for a sensor as set forth in claim 6, wherein, at the final stage of the operation of closing the outer cover, the positioning release means forcibly moves the mounting member to disengage the engagement shaft from one of the engagement portions, said one engagement portion being one with which said engagement shaft is engaged when said mounting member is moved in close to the enzyme electrode unit.

8. An apparatus for mounting a diffusion-limiting membrane for a sensor as set forth in claim 6, wherein, by sliding the positioning release means, the closed state of the outer cover is released and the swing member is forcibly swung to disengage the engagement shaft from one of the engagement portions, said one engagement portion being one with which said engagement shaft is engaged when said mounting member is moved in close to the enzyme electrode unit.

9. An apparatus for mounting a diffusion-limiting membrane for a sensor as set forth in claim 3, further comprising an insertion/removal preventive means adapted to be engaged with the diffusion-limiting membrane holding plate when the mounting member for mounting a diffusion-limiting membrane holding plate is moved toward the enzyme electrode unit.

10. An apparatus for mounting a diffusion-limiting membrane for a sensor as set forth in claim 9, wherein the mounting member for mounting a diffusion-limiting membrane holding plate is further provided in the groove thereof with a through-hole, and the insertion/removal preventive means is a pulling preventive shaft disposed on the sensor such that said shaft is adapted to project on said groove through said through-hole when said mounting member is moved toward the enzyme electrode unit.

11. An apparatus for mounting a diffusion-limiting membrane for a sensor as set forth in claim 3, further comprising a release mechanism for releasing a moving range limiting state provided by the positioning member.

12. An apparatus for mounting a diffusion-limiting membrane for a sensor as set forth in claim 11, wherein the positioning member is a swing member having a guide groove engaged with an engagement shaft disposed on the mounting member for mounting a diffusion-limiting membrane holding plate, said guide groove having a pair of engagement portions aligned with the swing center of said swing member, and the release mechanism is adapted to move said swing member in such direction that said engagement shaft is disengaged from said guide groove.

13. An apparatus for mounting a diffusion-limiting membrane for a sensor as set forth in claim 12, further comprising a lever normally biased toward the engagement shaft, said lever having the swing member.

14. An apparatus for mounting a diffusion-limiting membrane for a sensor as set forth in claim 11, wherein the release mechanism is operable from the outside of the lower, surface of the sensor.

15. An apparatus for mounting a diffusion-limiting membrane for a sensor as set forth in claim 3, further comprising:

an outer cover to be opened and closed, said outer cover being positioned so as to be opposite to the enzyme electrode unit when said cover is closed; and an inner cover adapted to be moved in association with the operation of opening/closing said outer cover, said inner cover being adapted to cover at least a portion of said enzyme electrode unit when said outer cover is opened.

16. An apparatus for mounting a diffusion-limiting membrane for a sensor as set forth in claim 15, wherein the inner cover is further provided with a large-diameter opening adapted to be opposite to the enzyme electrode unit when the outer cover is closed, and the outer cover is further provided with a wetting liquid holding portion adapted to come in contact with said enzyme electrode unit when the outer cover is closed.

17. An apparatus for mounting a diffusion-limiting membrane for a sensor as set forth in claim 15, wherein the outer cover is rotatable with respect to the sensor and the inner cover is slidable with respect to the sensor, and wherein there is further disposed links for connecting said outer cover to said inner cover 18. An apparatus for mounting a diffusion-limiting membrane for a sensor as set forth in claim 17, wherein the mounting member for mounting a diffusion-limiting membrane holding plate is further provided with guide grooves, and the inner cover is further provided with projections engaged with said guide grooves, said projections being connected to said outer cover with the links.

19. An apparatus for mounting a diffusion-limiting membrane for a sensor as set forth in claim 15, further comprising a regulating mechanism permitting the inner cover to be moved in a direction away from the mounting member for mounting a diffusion-limiting membrane holding plate, only when said inner cover receives an upwardly moving force greater than a predetermined amount.

20. An apparatus for mounting a diffusion-limiting membrane for a sensor as set forth in claim 19, wherein the regulating mechanism is constituted by projections which are projectingly formed on the inner cover at predetermined positions thereof.

21. An apparatus for mounting a diffusion-limiting membrane for a sensor as set forth in claim 19, wherein the regulating mechanism is constituted by projections which are projectingly formed on the sensor at predetermined positions thereof.

22. An apparatus for mounting a diffusion-limiting membrane for a sensor as set forth in claim 19, wherein the regulating mechanism permits the inner cover to be sufficiently moved upward only when said inner cover directly receives an upwardly rotating force greater than a predetermined amount.

23. An apparatus for mounting a diffusion-limiting membrane for a sensor as set forth in claim 19, wherein the regulating mechanism permits the inner cover to be sufficiently moved upward only when the outer cover is opened by an angle exceeding a predetermined angle.

24. An apparatus for mounting a diffusion-limiting membrane for a sensor comprising:

a pair of positioning portions disposed on a sensor having an enzyme electrode unit, said sensor also having an enzyme-immobilized membrane, said pair of positioning portions being opposite to each other with respect to said enzyme electrode unit;

a resilient thin plate adapted to be engaged with said pair of positioning portions, causing said resilient thin plate to resiliently bend to conform to the curvature of said enzyme electrode unit;

said resilient thin plate having an opening in the position thereof which is adapted to be opposite to said enzyme electrode unit; and said opening being covered by a diffusion-limiting membrane secured to said resilient thin plate and one of said pair of positioning portions being immovably attached to the sensor, while the other of said pair of positioning portions is vertically movably attached to the sensor.

* * * * *